United States Patent [19]

Kundin

[11] Patent Number: 4,483,075
[45] Date of Patent: Nov. 20, 1984

[54] APPARATUS AND METHOD FOR MEASURING DEFORMED AREAS OF SKIN SURFACE

[76] Inventor: Jane I. Kundin, 1288 Laurel Hill Dr., San Mateo, Calif. 94402

[21] Appl. No.: 503,067

[22] Filed: Jun. 10, 1983

Related U.S. Application Data

[63] Continuation-in-part of Ser. No. 343,890, Jan. 29, 1982, abandoned.

[51] Int. Cl.³ .......................... G01B 1/28; G01B 3/14; G01B 5/18
[52] U.S. Cl. .................................. 33/121; 33/169 B; 33/174 R
[58] Field of Search .................... 33/174 R, 121, 1 V, 33/169 B, 191; 128/630

[56] References Cited

U.S. PATENT DOCUMENTS

| | | | |
|---|---|---|---|
| 1,142,423 | 6/1915 | Hawthorne | 33/121 |
| 1,373,367 | 3/1921 | Summers | 33/191 |
| 1,780,237 | 11/1930 | Leslie | 33/121 |
| 3,955,073 | 5/1976 | Carew et al. | 33/1 V |
| 4,131,998 | 1/1979 | Spears | 33/121 |
| 4,216,585 | 8/1980 | Hatter | 33/169 B |
| 4,321,752 | 3/1982 | Kaufman | 33/169 B |

Primary Examiner—Willis Little
Attorney, Agent, or Firm—Limbach, Limbach & Sutton

[57] ABSTRACT

A novel apparatus and method for using the same is disclosed for determining the height and volume of a hematoma structure on the skin surface and for further determining the depth and area of a wound, particularly a crater-type wound on the skin's surface. The apparatus is primarily constructed with a first elongated member having incremental markings thereon and a second member having four radially outward extending arms with incremental markings thereon throughout the length of the radially extending arms where adjacent arms are disposed at 90 degrees angles from one another and a first and second member engaged one to the other and disposed perpendicularly. One embodiment of the invention is constructed of a single member comprising four flat, radially extending arms with incremental markings throughout the length of the arm and where the adjacent arms are disposed 90 degrees from one another. This embodiment of the invention is particularly suitable for measuring the height and volume of the hematoma structure.

14 Claims, 5 Drawing Figures

APPARATUS AND METHOD FOR MEASURING DEFORMED AREAS OF SKIN SURFACE

DESCRIPTION

This application is a continuation-in-part of my copending application Ser. No. 343890, filed Jan. 29, 1982 and entitled Wound Measurement Apparatus and Method for Using Same, now abandoned.

TECHNICAL FIELD

This invention relates to a medical apparatus for determining the depth, height and volume of certain segments of the skin's surface.

BACKGROUND ART

In the past there has been a distinct desire to be able to accurately measure the volume of certain areas of the skin surface such as an open cavity or crater-type wound which was created by the removal of a substantial amount of flesh and underlying muscle tissue, or fatty material. There has been a need to accurately determine the volume of these wounds to determine if there was proper granulization of the flesh and underlying muscle and if proper healing was taking place.

In cases where there are the above described wounds, the healing process is long. The changes in the wound from day-to-day appear minimal. However, if there is an accurate means by which to measure the wound volume at a specific point in time, there can be a determination whether the proper granulization was taking place to effect healing.

In the past there has been no specific apparatus and method for using same to be able to properly calculate the volume of an open wound of the type previously described. As such, doctors and medical personnel had to guess at the amount of progress that was taking place for the healing of the wound.

There are certain prior art apparatuses which may be utilized to determine dimensions of certain segments of the body's surface. For example, the apparatus disclosed in U.S. Pat. No. 4,321,752 (Kaufmann) discloses an apparatus which is capable of measuring only the depth of a segment of the skin surface in relation to the surface of the abdomen. The apparatus is particularly suitable for determining the percentage of fat in a human body. The '752 apparatus could not be utilized to derive the measurements needed to determine the volume of a crater-type wound. That is, that apparatus would not be capable of measuring the depth of the wound in relation to the length and width of the surface opening of the wound to give the measurements needed for determining the volume of the wound. The apparatus of the present invention solves this problem.

Another prior art apparatus used to measure certain dimensions of the skin is disclosed in U.S. Pat. No. 4,131,998 (Spears). The '998 apparatus is used to measure the two dimensional sides of a round tumor growth. From this estimate, a growth rate of tumor volume is estimated. The Spears method is quite limited in scope and is of questionable reliability in estimating volumes and growth rates of tumors. Unlike the Spears apparatus, the present apparatus is more sensitive to irregularly shaped structures (not just round tumors), and since three-dimensional measurements are given, a much more accurate estimate of the structure's volume can be obtained. The Spears apparatus is unable to measure either height or depth of a surface area.

Still another apparatus which may have some applicability in the area of measuring the dimensions of certain surface areas is taught is U.S. Pat. No. 1,373,367 (Summers). The device of '367 patent is able to find the exact center of a square or circular segment of the body's surface which has a flat surface. Perhaps the Summers device, with the proper mathematical formula, could be utilized to measure the area of a flat square or circle. Again, and like the Spears apparatus and, to a lesser extent, the Kaufmann apparatus, the Summers device would have very little, if any, use in determining the dimensions of an irregular-shaped surface, and in no event would this device be able to supply a three-dimensional measurement. The Summers device does not at all appear to be suitable for measuring skin surfaces on the human body.

The present invention overcomes these problems and provides an apparatus and method for using same to be able to accurately determine not only the volume of a crater-type wound and be able to monitor the granulization process in the course of healing, but to determine the volume of other deformed areas on the skin surface such as hematomas.

SUMMARY OF THE INVENTION

The present invention is an apparatus and method by which the volume of a crater-type wound or other deformed area on the skin surface can be continually monitored to make certain vital determinations about the areas such as if proper granulization of the flesh and underlying muscle is taking place in the case of an open wound. Also, in the case of a hematoma an increase or decrease in its volume can be used to make certain determinations about the hematoma such as its rate of growth and the estimated volume of blood loss due to the growth.

The invention represents a cartesian, rectangular, three dimensional coordinate system which can be imposed onto different, often irregularly shaped, structures of the body to obtain measurements which can be easily applied to formulas of conventional mathematical models to derive areas, volumes and other information about the structures or segments of skin surface measured. Successive measurements will give valuable information about growth rates and other processes as they occur.

The apparatus is inexpensive, consistent, accurate, non toxic and can be easily sterilized without loss of shape or accuracy. Its use does not require the patient be moved or subjected to discomfort or risk. Its use requires a minimum of medical staff time and gives objective information of the patient's condition for clinical as well as research purposes.

The primary embodiment of the invention consists of a first and second member which slidably engage each other and are disposed perpendicularly. The first member is a strip of material having measurement markings disposed along the entire longitudinal length. The second member is a single piece of material consisting of four radially outward extending arms where adjacent arms are disposed 90° to each other.

The radially extending arms meet at a center point of the second member. Each of the arms has incremental measurement markings throughout their length. The center point, where all the arms meet, serves as the zero point for the measurement markings throughout the length of the respective arms. Also disposed at the center of the second member is a circular portion which has incremental degree markings disposed at the periphery of the circular portion.

Each of the arms has thereon disposed a set of markings distinct from that of the other arms. The distinctive markings on the respective arms are used to distinguish the arms so that there is proper orientation of the apparatus when used for subsequent measurements of the wound.

The first member of the primary embodiment slidably engages the second member at the center. As previously stated, when the first and second member are in slidable engagement, the two members are perpendicular to each other.

When the apparatus is used to measure a wound, the first member is slid through the second member until the end of the first member contacts the deepest part of the wound and the second member is arresting on the skin surface. When the first member is slid through the second member there can be a determination of the depth of the crater of the wound by an indication of depth on the scale on the first member.

The open area of the crater at the skin surface can be determined by a measurement of the open area by using the second member. The measurements of the open area are where each of the arms cross the edges of the open area. Any unusual characteristics of the wound can be determined by their location in respect to the degree markings on the center portion of the second member.

When in use the above described apparatus is generally aligned in the same manner each time the apparatus is used on one particular would to make measurements for calculating the volume of the wound. A consistent orientation is always necessary so that data is more meaningful for comparison and the unusual characteristic section of the wound can be documented and observed as to its healing.

The object of the invention is to provide an apparatus for measuring the depth and surface area of certain deformed areas of the skin surface such as hematomas and wounds in order to determine the volume of the area by utilizing an appropriate mathematical model.

DETAILED DESCRIPTION OF THE DRAWINGS AND PREFERRED EMBODIMENTS

Figure 1:
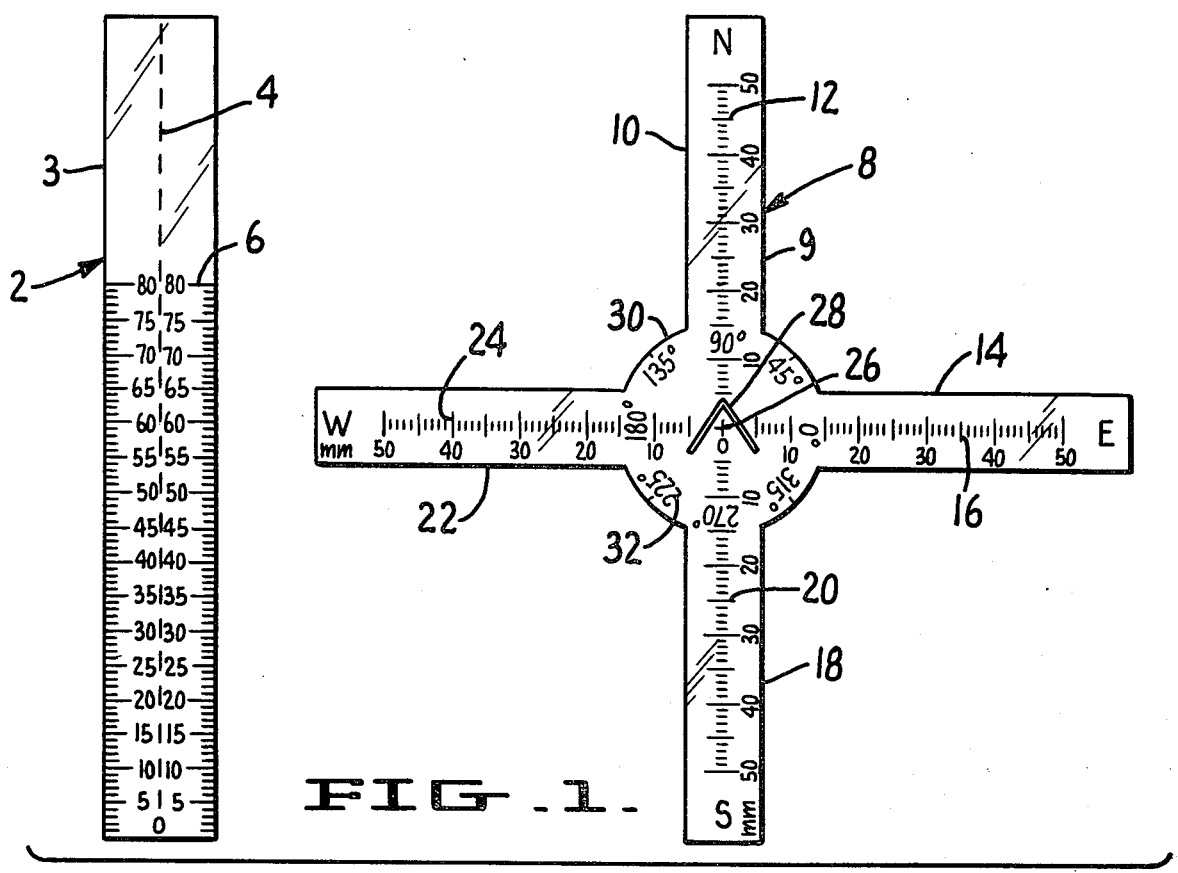
FIG. 1 shows a plane view of the two members which comprise the apparatus for providing measurements to determine the volume of an area on the skin's surface.

FIG. 1 shows first and second members of the apparatus used to make measurements to determine the volume of the crater-type wound.

Shown in FIG. 1 generally at 2 is the first member of the above described apparatus. The first member 3 is elongated and generally of a rectangular shape. The first member 3 has a fold line which extends the entire longitudinal length of member 3 and is generally located at the longitudinal center line of member 3. The elongated member 3 has thereon disposed incremental markings printed along the entire longitudinal length of first member 3. The markings can be in millimeters, inches or any other conventional measurement scale. One end of member 3 is the zero point. From the zero point the incremental markings are marked with progressively larger numbers until such markings reach an end opposite the one having the zero marking.

The second member of the apparatus is generally shown at 8. In the primary embodiment of the invention, the second member consists of arms 10, 14, 18 and 22. The second member is of one piece construction. But it can be constructed of separates that are joined. The arms meet at or about center point 26 such that each adjacent arm is disposed 90° from the other. Disposed at the geographic center of the arms is a circular portion 30 of the second member 9. The arms 10, 14, 18 and 22 are generally of an elongated rectangular shape. When the arms 10, 14, 18 and 22 are so joined, they are all generally in the same plane. Also the center circular portions 30 is in the same plane as arms 10, 14, 18 and 22.

The arms at 10, 14, 18 and 22 have incremental markings 12, 16, 20 and 24, respectively. The incremental marking on arms 10, 14, 18 and 22 have a zero point at center point 26. From the center point 26 the incremental markings are marked with progressively larger numbers from said zero point 26 to a point near the end of respective arms. Each of the arms has a distinctive marking which is different from the other arms. In this case arm 10 is marked with a "N" to represent north; arm 14 is marked with a "E" to represent east; arm 18 is marked "S" to represent south; and arm 22 is marked with a "W" to represent west. The nature of the unique markings is to allow for proper orientation of the apparatus for each use in making measurements to determine the area of a flat wound or volume of a hematoma or a crater-type wound.

Center circular portion 30 has incremental degree markings 32. The incremental degree markings 32 have a zero point along the axis of the center of the "E" arm (arm 14). The degree markings are used to determine the position of any unique features of the surface area to be measured so that progress can be recorded as to changes of the characteristics of the area such as a wound.

Disposed about center 26 of second member 9 is a V-shaped slit 28. The V-shaped slit 28 is provided to accommodate the slidable engagement of first member 3. When it is desired to use the apparatus, the first member 3 is folded along fold line 4 and slid into V-shaped slit 28 of second member 9. The first member can easily be slid in and out of second member 9 in directions "A" and "B" as shown.

Although V-shaped slit 28 is shown in all of the Figures as the means at which and by which first member 3 and second member 9 are engaged, the inventor does not contemplate this to be the only engaging means for the first member 3 and second member 9. The first member 3 can also be constructed in a circular pattern having threads disposed throughout the whole length and having incremental markings also disposed throughout the entire length of first member 3. In such case, the second member 9 would not have slit 28, but would be adapted to receive threaded member 3 in a screw/nut relationship. Instead of first members sliding into second member 9, it would threadably engage member 9. The inventor, thus, contemplates other conventional means for the engagement of members 3 and 9.

The first member 3 and second member 9 can be constructed of various materials. They can be constructed of plastic coated paper and various types of plastic which are rigid or semi-rigid. The use of paper allows for disposal after use and aids in the control of infections. In the preferred embodiment of the invention the apparatus is constructed of a clear plastic material and both members are flexible. The flexibility is of particular interest in the construction of second member 9. The flexibility of second member 9 is desired because when the apparatus is measuring the open area of a crater type wound, it will be easier to make an accurate measurement if the arms can deform to the contour of the body surrounding the crater type wound. This flexibility is also desirable in measuring hematomas. It is not as essential to have first member 3 constructed of a flexible material as it is for second member 9. All that is necessary in the area of flexibility for first member 3, is that it must be able to be easily folded along fold line 4 such that it can be slid into V-shaped slit 28 of second member 9.

In the primary embodiment and particularly when the apparatus is used for wound measurements, it is probably most desirable to have both first member 3 and second member 9 constructed of a clear semi-rigid plastic. If the apparatus is so constructed it will not absorb body fluids and will still provide for an easy means to make all measurements necessary for determining the volume of a wound or other surface since the members will be able to follow the contour of the skin area surrounding the crater type wound. While a plastic material can be utilized in a device for measuring flat wounds and hematomas it should be borne in mind that the actual material used for the device can vary with the specific application. Thus, in certain instances (such as measuring hematomas) a less costly material can be used.

Figure 2:
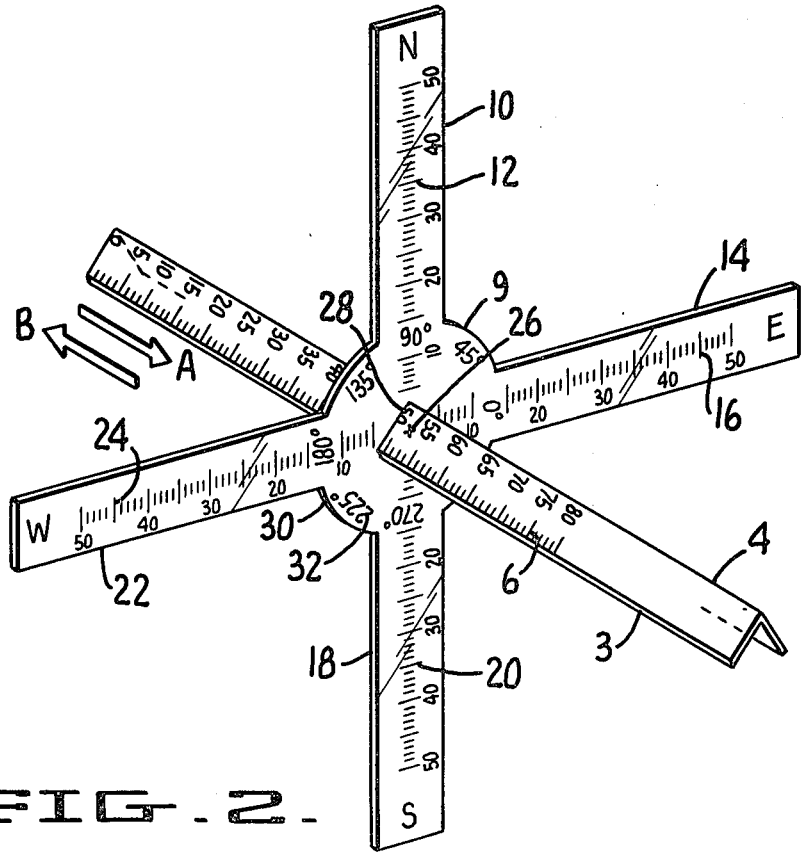
FIG. 2 shows the wound measurement apparatus in which the first and second members are engaged.

FIG. 2 shows second member 9 with first member 3 therein disposed. First member 3 can move in direction "A" or "B" when used to measure the depth of a crater-type wound. The remainder of the apparatus is as described previously for FIG. 1.

Figure 3:
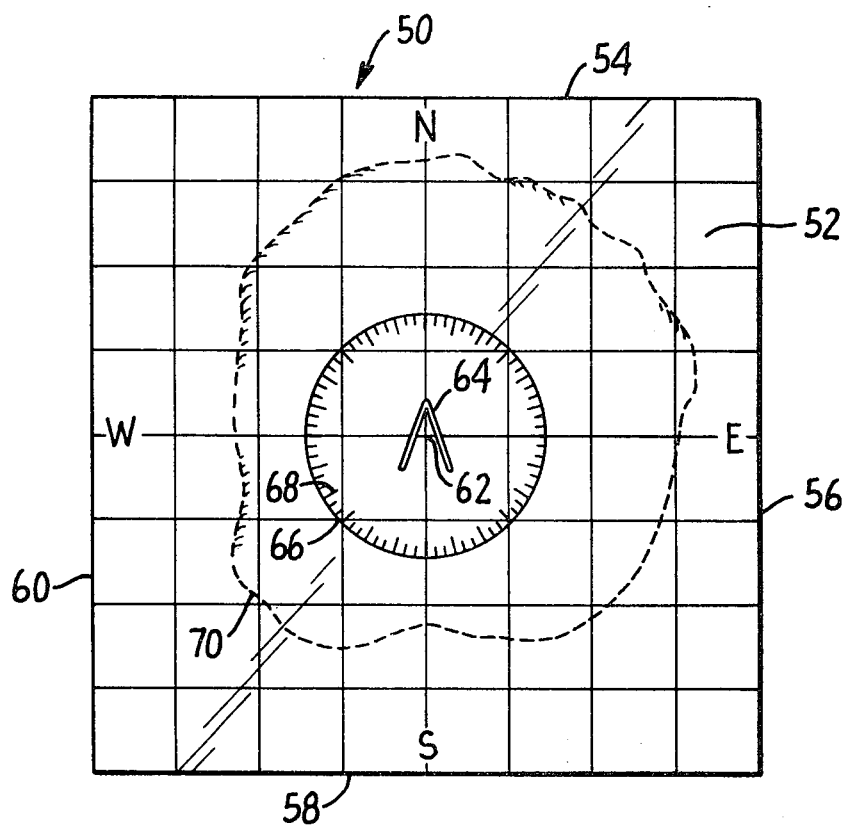
FIG. 3 shows a second embodiment of the second member of the apparatus.

FIG. 3 shows the second embodiment of the second member of the apparatus, generally shown at 50. The second member 54 may be constructed of a clear plastic and has printed thereon a grid 52. Each of the sides of the grid has a distinctive marking which is used for orientation of the second member for making consistent measurements of the open area of the crater-type wound. The orientation is a significant factor for accurate measurements over a long period of time. The orientation is also necessary for being able to monitor the specific characteristics of the wound noted at specific locations identified by their position in respect to the center portion 66 having incremental degree markings 68. The sides 54, 56, 58 and 60 are generally of the same size, however, any rectangular representation is proper for the invention. The grid system allows for a fairly easy determination of an open area at the surface of the skin of a crater-type wound generally represented by phantom lines 70.

Center 62 of grid 52 has disposed about it V-shaped slit 64 which is used to receive the folded first member. Second member 52 is, as was for the primary embodiment, constructed of a clear flexible plastic type material. This is necessary so that it can flex with the contour of the body member for accurate measurements of the area of the opening of the crater-type wound.

Figure 4:
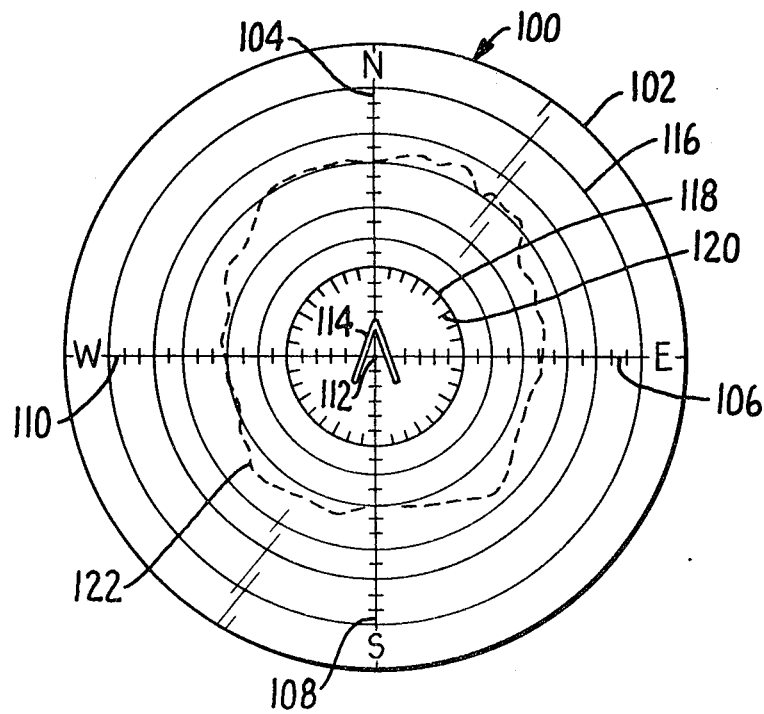
FIG. 4 shows a third embodiment of the second member of the apparatus.

FIG. 4 generally at 100 shows the third embodiment of the second member of the apparatus. The second member 102 is generally of circular construction. From center point 112 there are sector dividing lines 104, 106, 108 and 110. These sector lines divide the circular member 102 into four separate quadrants. At extreme ends of the section line there are unique markings which are different for each of the lines. Disposed from the center 112 are concentric circles 116. The concentric circles 116 emanate from center 112 and increase in diameter out to the outer perimeter of second member 102.

The concentric circles 116 provide another easy method in which to make a determination of the area of the opening of the wound shown by phantom lines 122.

One of the concentric circles 118 has incremental degree markings 120. This circle serves as center portion as described for the previous embodiments. The circular portion 118 is used to determine the locations of specific characteristics of the wound or other skin surface area being measured and provides means by which the characteristics can be identified and cataloged for future reference. As the wound is healing and the apparatus is being used for determining wound volume, the apparatus will be properly aligned or oriented for subsequent measurements of the wound and the unique characteristics.

The method of using the apparatus will be described for the primary embodiment in the following, however, the same theory of operation will apply to all embodiments of the invention.

When it is desired to make the measurement to determine the the area of a flat wound or the volume of a crater-type wound or hematoma, first member 3 is inserted through V-shaped slit 28 of member 9. First member 3 can be slid in either direction "A" or "B". When in use for measuring the depth of a wound, the apparatus is placed in the wound such that the zero end of first member 3 contacts the deepest part of the crater-type wound and second member 9 is slid along first member 3 until it contacts the surface of the skin around the crater type wound. The arms of the second member 9 are oriented about the wound. The depth of the wound is determined by the indication of the depth along the incremental marking scale of first member 3. The depth is read where the first member 3 and second member 9 intersect.

After the depth has been determined it is necessary to make the measurements to determine the area of the opening of the crater-type wound at the skin surface.

To make such measurement of the surface area of the opening, the measurements are made along arms 10, 14, 18 and 22 specifically where the arms cross the edges of the crater-type wound. Then measurement is read off of the scales 12, 16, 20 and 24, respectively. The readings from the scales 10, 14, 18 and 22 are input into a formula along with the depth measurement to calculate the volume of the crater-type wound.

Once the wound volume is calculated, all subsequent volumes will be compared with this initial volume. Comparison of the volumes taken over a period of time will indicate whether the wound is properly healing. Also, the effectiveness of different treatments can be compared by comparing measured rates of healing of different wounds.

When the apparatus is configured to use the second embodiment of the second member (FIG. 3), the same method of obtaining a depth of the wound is used. The difference is the way in which the area of the opening of a wound in the flesh surface is determined. When this embodiment of the second member is used to determine the area of the opening, the area subtended by the wound grid is what is used as the area input to the calculation for determining the volume.

When the apparatus is configured utilizing the third embodiment of the second member, the same method determining the depth of the wound as previously described for the other embodiments is used. The area of the opening is determined by use of the concentric circles printed on member 102. Once the area is determined, it is easy to calculate the volume of the wound the first and subsequent times when measurements are taken.

When the apparatus of the invention is used to measure the dimensions of a hematoma or lump in order to determine any increase or decrease in the volume of the hematoma and thereby determine the volume of any blood or other fluid under the surface of the skin in the area of the hematoma, only the second member of the apparatus (generally shown at 8 in FIG. 2) is used in detecting the measurements. Member 8 is centered about the top surface area of the hematoma with point 6 centered on the top surface of the lump. Radial arms 10, 14, 18 and 22 are extended at right angles over the surface of the hematoma area. The hematoma measurements along each of the arms 10, 14, 18 and 22 are recorded, thus giving the length of the curved surface of the hematoma or lump in the NORTH-SOUTH (N-S) and EAST-WEST (E-W) directions, respectively. These distances are subsequently measured with calipers to give the straight distances between the same two end points in each direction. These four distances (two curved and two flat) are applied to suitable formulas of the elliptical mathematical model to derive the height, area, and volume of the hematoma area. These measurements can be periodically taken and recorded and applied to the elliptical formula to determine the increase or decrease in the hematoma growth.

Oftentimes, patients are injected with certain necessary drugs which often result in a hematoma structure forming at the injection site. Different methods of injection of a particular drug may cause variable amounts of blood and other fluids to accumulate under the patient's skin. Determining the resulting effect of the various injection methods, i.e. the amount of blood and other fluid accumulating under the skin surface, is desirable. The apparatus of the invention can be used to determine the dimensions necessary to study the effects of the various injection methods.

Figure 5:
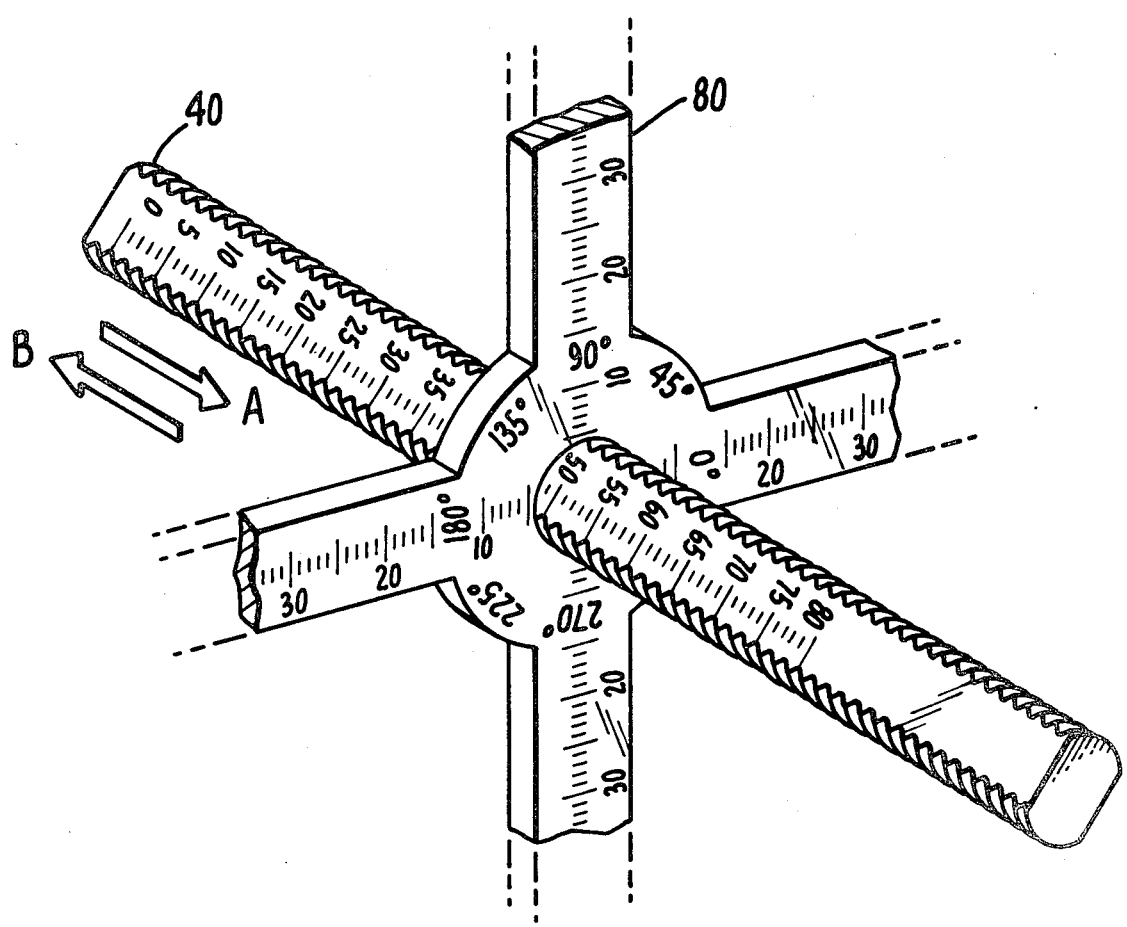
FIG. 5 illustrates still a further embodiment of applicant's invention.

FIG. 5 illustrates an embodiment of the invented apparatus wherein a first member 40 threadably engages second member 80. The FIG. 5 apparatus may be constructed of a more rigid material (such as stainless steel) than the previously described apparatuses and may be suitable for application in forensic medicine where neither the comfort nor infections to the patient are of concern.

Although it is not shown in the drawings, the apparatus of the invention, used to make measurement to determine the volume of a hematoma or a crater-type wound, can be configured such that the first and second members have means connected to input sections to the computer. This will allow an automatic determination of the wound volume once the readings are made. In this embodiment the first and second members would have sensing means such that there can be determination where a first member and a second member intersect to provide input to the computer for depth and second there can be means by which the area of the opening can be detected by sensing means along the arms of the second member. These sensing means will provide the necessary inputs for depth and area for calculation of volume. Once these inputs are made, there can be a read-out of the volume of the crater-type wound. This method would probably be the most accurate in which to determine the volume of the crater-type wound during the healing process.

The inventor contemplates the invention to be all that is shown, described, and claimed to be an invention. However, there can be various adaptations and alterations to the apparatus as to what is shown, described and claimed so the inventor contemplated the invention to be all that is shown, described and claimed in all points thereto.

I claim:

1. An apparatus for measuring a portion of skin surface comprising:
    a first elongated member having incremental markings thereon;
    a second member having four flat, flexible, radially-extending arms, each having incremental markings thereon with adjacent arms being disposed at an angle of substantially 90 degrees from one another and with all of said arms extending from a circular center portion having degree markings thereon, and wherein said first member engages said second member with said first member being disposed substantially perpendicular to said second member, such that the first member measures the depth of said surface portion and said second member measures the area of same surface portion.

2. The apparatus as recited in claim 1 wherein the first member slidably engages the second member.

3. The apparatus as recited in claim 1 wherein the first member threadably engages the second member.

4. The apparatus as defined in claim 1 wherein said circular center portion has a center point from which all of said incremental markings begin.

5. The apparatus as recited in claim 1 wherein the second member further comprises a flat flexible grid with incremental markings thereon and having a circular center portion having degree markings thereon.

6. The apparatus as recited in claim 1 wherein the second member further comprises a flat flexible member having concentric circular ring markings and a circular portion with degree markings thereon.

7. A method of determining the volume of a wound comprising:
    measuring a depth and an area of a surface opening of an open wound with an apparatus comprising a first elongated member having incremental markings for measuring depth and a second member which has engagement means for slidably engaging the first member having measuring means for determining the area of a surface opening; and
    computing a wound volume from the depth indicated by said first member and surface area of the wound opening by said second member.

8. The method as recited in claim 7 wherein the first member is disposed perpendicular to the second member.

9. The method as recited in claim 8 wherein the second member further comprises four flat flexible radially outward extending arms each having incremental markings thereon and adjacent arms are disposed at an angle of 90 degrees from one another and having a circular center portion having incremental degree markings thereon for indicating a position of characteristics of the wound relative to a predesignated position on said second member.

10. The method as recited in claim 7 wherein the second member further comprises a flat flexible member having a grid with incremental markings and having a circular center portion having incremental degree markings for indicating a position of characteristics of the wound relative to a predesignated position on said second member.

11. The method of claim 7 wherein the second member further comprises a flat flexible member having concentric circular ring markings and a circular center position having incremental degree markings for indicating a position of characteristics of the wound relative to a predesignated position on said second member.

12. A method of determining the volume of a hematoma structure on the surface of the skin comprising the following steps:
determining the height of said hematoma structure with an apparatus comprising four flat, flexible, radially extending arms, each having incremental markings thereon and adjacent arms disposed at an angle of 90 degrees from one another;
extending the NORTH-SOUTH axis of said apparatus along the longest axis of said hematoma structure and extending the EAST-WEST axis along the shorter axis of said hematoma structure;
measuring the distance along the NORTH-SOUTH and EAST-WEST axes of said hematoma structure;
measuring the straight distance along the NORTH-SOUTH and EAST-WEST axes of said hematoma structure with a pair of calipers;
applying the distances along the NORTH-SOUTH axis and the EAST-WEST axis computed using said apparatus and the same distances along the same axes computed using said calipers to the formula for determining the perimeter of an elliptical mathematical model to derive the height of said hematoma structure; and
applying the height dimension, the distance along the hematoma's NORTH axis, SOUTH axis, EAST and WEST axes respectively, measured by said apparatus, and the straight distances along the NORTH-SOUTH and EAST-WEST axes of said hematoma structure measured with said calipers to formulas for determining the volume of an elliptical mathematical model to derive the volume of said hematoma structure.

13. The method as recited in claim 11 wherein said apparatus further comprises a circular center portion having degree markings thereon.

14. The method as recited in claim 12 wherein said circular center portion has a center point from which all of said incremental markings begin.

* * * * *